(12) United States Patent
Tokumasu

(10) Patent No.: US 6,423,876 B1
(45) Date of Patent: Jul. 23, 2002

(54) PROCESS FOR PRODUCING DIHYDROXYBENZENE

(75) Inventor: Shigefumi Tokumasu, Kisarazu (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/062,724

(22) Filed: Feb. 5, 2002

(30) Foreign Application Priority Data

Jun. 8, 2001 (JP) .......................................... 2001-173726

(51) Int. Cl.⁷ .......................... C07C 27/10; C07C 29/10; C07C 35/04

(52) U.S. Cl. ................................................... 568/700

(58) Field of Search ......................................... 568/768

(56) References Cited

U.S. PATENT DOCUMENTS

| | | | | |
|---|---|---|---|---|
| 2,748,172 A | * | 5/1956 | Rodgers | |
| 3,798,277 A | * | 3/1974 | Sugiyama | |
| 4,229,569 A | * | 10/1980 | Burkholder | |
| 4,273,623 A | * | 6/1981 | Hashimoto | |
| 4,283,567 A | * | 8/1981 | Nambu | |
| 4,434,305 A | * | 2/1984 | Kurosaka | |

* cited by examiner

Primary Examiner—Michael L. Shippen
(74) Attorney, Agent, or Firm—Sughrue Mion, PLLC

(57) ABSTRACT

There is provided a process for producing dihydroxybenzene, which comprises the steps of:

(1) oxidizing diisopropylbenzene to obtain a reaction mixture containing di(2-dihydroperoxy-2-propyl)benzene;

(2) cleaving di(2-dihydroperoxy-2-propyl)benzene in the reaction mixture to obtain a mixture containing crude dihydroxybenzene;

(3) distilling the mixture containing crude dihydroxybenzene to obtain a fraction containing acetone from a low boiling side, and a fraction containing dihydroxybenzene from a high boiling side;

(4) distilling the fraction containing dihydroxybenzene obtained in the above-mentioned step (3) to obtain a fraction containing dihydroxybenzene from a low boiling side, and a fraction containing heavy material from a high boiling side; and (5) mixing the fraction containing dihydroxybenzene obtained in the above-mentioned step (4) with water, and contacting the resulting mixture with an extraction solvent, followed by separating into an aqueous layer containing dihydroxybenzene and an oily layer containing impurity.

5 Claims, 1 Drawing Sheet

PROCESS FOR PRODUCING DIHYDROXYBENZENE

FIELD OF THE INVENTION

The present invention relates to a process for producing dihydroxybenzene. More specifically, the present invention relates to a process for producing purified dihydroxybenzene, which is superior from an operational point of view because of absence of a step of handling a solid, and which has no need of using any additive to improve liquid separability in an extraction step.

BACKGROUND OF THE INVENTION

For example, JP-A 64-38 discloses a process for producing dihydroxybenzene, which comprises the steps of:

(1) oxidizing diisopropylbenzene to obtain a reaction mixture containing di(2-dihydroperoxy-2-propyl)benzene;

(2) cleaving di(2-dihydroperoxy-2-propyl)benzene in the reaction mixture to obtain a mixture containing crude dihydroxybenzene; and (3) obtaining purified dihydroxybenzene from the mixture containing crude dihydroxybenzene.

However, said process has a problem that purification by liquid separation is insufficient, and therefore it is necessary to use an additive to improve the liquid separability.

SUMMARY OF THE INVENTION

An object of the present invention is to provide a process for producing a purified dihydroxybenzene, which is superior from an operational point of view because of absence of a step of handling a solid, and which has no need of using any additive to improve liquid separability in an extraction step.

The present invention provides a process for producing dihydroxybenzene, which comprises the steps of:

(1) oxidizing diisopropylbenzene to obtain a reaction mixture containing di(2-dihydroperoxy-2-propyl)benzene;

(2) cleaving di(2-dihydroperoxy-2-propyl)benzene in the reaction mixture to obtain a mixture containing crude dihydroxybenzene:

(3) distilling the mixture containing crude dihydroxybenzene to obtain a fraction containing acetone from a low boiling side, and a fraction containing dihydroxybenzene from a high boiling side;

(4) distilling the fraction containing dihydroxybenzene obtained in the above-mentioned step (3) to obtain a fraction containing dihydroxybenzene from a low boiling side, and a fraction containing heavy material from a high boiling side; and (5) mixing the fraction containing dihydroxybenzene obtained in the above-mentioned step (4) with water, and contacting the resulting mixture with an extraction solvent, followed by separating into an aqueous layer containing dihydroxybenzene and an oily layer containing impurity.

BRIEF DESCRIPTION OF THE DRAWINGS

In FIG. 1, respective numerals mean the followings:

Figure 1:
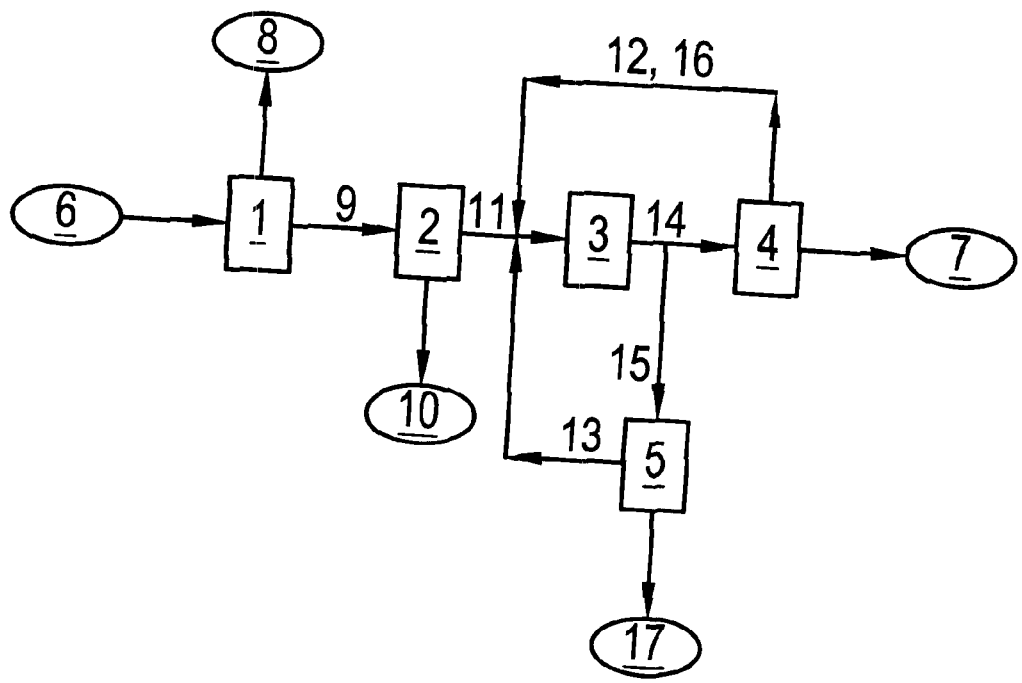
FIG. 1 is a flow chart showing the process in accordance with the present invention.

1: step (3), 2: step (4), 3: step (5), 4: step (6), 5: an extraction solvent recovery step, 6: a mixture containing crude dihydroxybenzene, 7: purified dihydroxybenzene, 8: a fraction containing acetone from a low boiling side, 9: a fraction containing dihydroxybenzene from a high boiling side, 10: a fraction containing a heavy material from a high boiling side, 11: a fraction containing dihydroxybenzene from a low boiling side, 12: water, 13: an extraction solvent, 14: an aqueous layer containing dihydroxybenzene, 15: an oily layer containing isopropenylphenol (an extraction solvent layer), 16: a fraction containing dihydroxybenzene, and 17: a fraction containing isopropenylphenol.

DETAILED DESCRIPTION OF THE INVENTION

Steps (1) and (2) of the present invention may be those known in the art.

The mixture containing crude dihydroxybenzene obtained in step (2) of the present invention contains usually from 2 to 40% by weight of dihydroxybenzene, usually from 2 to 40% by weight of acetone, and usually from 0.01 to 5% by weight of isopropenylphenol, provided that the total amount of said mixture is 100% by weight. In some cases, the mixture may further contain methyl isobutyl ketone and acetylphenol.

As a distilling method in step (3), there is exemplified a method of distilling under a condition of −95 to 1000 KpaG using a rectifying tower. A fraction from a low boiling side obtained according to said method contains usually from 2 to 80% by weight of acetone, provided that the total amount of said fraction is loot by weight; and a fraction from a high boiling side obtained contains usually from 70 to 99% by weight of the dihydroxybenzene, usually from 0.1 to 20% by weight of the isopropenylphenol and usually from 1 to 30% by weight of a heavy material, provided that the total amount of said fraction is 100% by weight.

As a distilling method in step (4), there is exemplified a method of distilling under a condition of −100 to 0 KpaG by means of simple distillation or with use of a rectifying tower. A fraction from a low boiling side obtained according to said method contains usually from 80 to 99.9% by weight of the dihydroxybenzene and usually from 0.1 to 20% by weight of the isopropenylphenol, provided that the total amount of said fraction is 100% by weight. A fraction from a high boiling side obtained contains a heavy material. In step (4), the heavy material can be decomposed to restore dihydroxybenzene.

As an extraction method in step (5), there is exemplified a method comprising the steps of (1) adding water to the fraction containing dihydroxybenzene to adjust a dihydroxybenzene concentration to from 5 to 70% by weight, and (ii) contacting the adjusted liquid with an extraction solvent in a countercurrent manner with use of an extraction tower or a mixer-settler extractor. According to said method, an aqueous layer containing dihydroxybenzene and an oily layer containing from 0.05 to 20% by weight of isopropenylphenol can be separated from each other. The extraction solvent is not particularly limited. Toluene is a preferable solvent from a viewpoint of extraction efficiency and separability.

As a distilling method in step (6), there is exemplified a method of distilling under a condition of −99 to 1000 KpaG using a rectifying tower. According to said method, it may be conducted that a fraction containing water is distillation-removed, and thereafter a fraction containing purified dihydrobenzene is obtained as a distillate. A light distillate containing dihydroxybenzene (a component heavier than water), and a heavy portion containing dihydroxybenzene, both of which are made in this step, can be recycled to any of steps (2) to (5).

EXAMPLE

Example 1 m-Diisopropylbenzene was oxidized to obtain a reaction mixture containing m-di(2-dihydroperoxy-2-propyl)benzene (step (1)); and m-di(2-dihydroperoxy-2-propyl)benzene in the reaction mixture was cleaved to obtain a mixture containing crude resorcinol (step 2). The mixture containing crude resorcinol was found to contain 10% by weight of resorcinol, 10% by weight of acetone, 0.5% by weight of m-isopropenylphenol and 70% by weight of methyl isobutyl ketone.

23 Parts by weight of the mixture containing crude resorcinol was distilled under a condition of −91 to 0 KpaG using a rectifying tower, thereby obtaining 20 parts by weight of a fraction containing 11% by weight of acetone from a low boiling side, and 2.5 parts by weight of a fraction containing 92% by weight of resorcinol, 1.5% by weight of m-isopropenylphenol and 6% by weight of a heavy material from a high boiling side (step (3)).

2.5 Parts by weight of the fraction from the high boiling side was distilled under a condition of −95 KpaG using a rectifying tower, thereby obtaining 2.3 parts by weight of a fraction containing 98% by weight of resorcinol and 1.5% by weight of m-isopropenylphenol from a low boiling side, and 0.2 part by weight of a fraction containing a heavy material from a high boiling side (step (4)).

To a mixture of 2.3 parts by weight of the fraction from the low boiling side and 0.2 part by weight of a fraction mainly containing resorcinol recycled from the below-mentioned step (6), water was added to adjust a resorcinol concentration in the resulting mixture to 50% by weight. Thereafter, the resulting mixture was subjected to liquid-liquid contact with 3 parts by weight of toluene (extraction solvent) in a countercurrent manner using a combination of an extracting tower and a mixer-settler extractor, thereby separating into 5 parts by weight of an aqueous layer containing 50% by weight of resorcinol, and 3 parts by weight of an oily layer containing 1% by weight of m-isopropenylphenol (step (5)).

5 Parts by weight of the aqueous layer containing 50% by weight of resorcinol was distilled under a condition of −96 to 350 KpaG using a rectifying tower in a manner such that a fraction containing water was distillation-removed and thereafter resorcinol was distilled out, whereby 2.3 parts by weight of a purified resorcinol was obtained (step (6)). 2.5 parts by weight of distilled water and 0.2 part by weight of a fraction containing resorcinol, which had been made in this step, were recycled to the above-mentioned step (5).

What is claimed is:

1. A process for producing dihydroxybenzene, which comprises the steps of:
   (1) oxidizing diisopropylbenzene to obtain a reaction mixture containing di(2-dihydroperoxy-2-propyl)benzene;
   (2) cleavinq di(2-dihydroperoxy-2-propyl)benzene in the reaction mixture to obtain a mixture containing crude dihydroxybenzenes;
   (3) distilling the mixture containing crude dihydroxybenzene to obtain a fraction containing acetone from a low boiling side, and a fraction containing dihydroxybenzene from a high boiling side;
   (4) distilling the fraction containing dihydroxybenzene obtained in the above-mentioned step (3) to obtain a fraction containing dihydroxybenzene from a low boiling side, and a fraction containing heavy material from a high boiling side; and
   (5) mixing the fraction containing dihydroxybenzene obtained in the above-mentioned step (4) with water, and contacting the resulting mixture with an extraction solvent, followed by separating into an aqueous layer containing dihydroxybenzene and an oily layer containing impurity.

2. The process for producing dihydroxybenzene according to claim 1, which comprises further step (6) of distilling the aqueous layer containing dihydroxybenzene obtained in the above-mentioned step (5) to separate into a fraction containing dihydroxybenzene and a fraction containing water.

3. The process for producing dihydroxybenzene according to claim 1, wherein diisopropylbenzene is m-diisopropylbenzene, and dihydroxybenzene is resorcinol.

4. The process for producing dihydroxybenzene according to claim 1, wherein the extraction solvent in step (5) contains toluene.

5. The process for producing dihydroxybenzene according to claim 1, wherein the mixture containing crude dihydroxybenzene is a mixture containing acetone, isopropenylphenol, methyl isobutyl ketone and a heavy material.

\* \* \* \* \*